United States Patent

Parks et al.

[11] 4,018,562
[45] Apr. 19, 1977

[54] CHEMILUMINESCENT NITROGEN DETECTION APPARATUS AND METHOD

[75] Inventors: Robert E. Parks, Houston; Robert L. Marietta, Richmond, both of Tex.

[73] Assignee: Antek Instruments, Inc., Houston, Tex.

[22] Filed: Oct. 24, 1975

[21] Appl. No.: 625,510

[52] U.S. Cl. .................. 23/230 PC; 23/230 M; 23/253 PC; 23/254 R
[51] Int. Cl.[2] ............... G01N 21/24; G01N 31/12; G01N 31/08
[58] Field of Search ......... 23/232 R, 232 E, 254 R, 23/254 E, 255 R, 255 E, 230 PC, 253 PC, 230 M; 73/23

[56] References Cited

UNITED STATES PATENTS

| | | | |
|---|---|---|---|
| 3,428,432 | 2/1969 | Stauton et al. | 23/253 |
| 3,518,059 | 6/1970 | Levy | 23/230 PC |
| 3,647,387 | 3/1972 | Benson et al. | 23/232 R |
| 3,718,429 | 2/1973 | Williamso, Jr. | 23/254 R |
| 3,838,969 | 10/1974 | Dugan | 23/230 PC |
| 3,847,546 | 11/1974 | Paul | 23/253 PC |
| 3,877,875 | 4/1975 | Jones et al. | 23/230 PC |
| 3,904,371 | 9/1975 | Neti et al. | 23/232 R |

Primary Examiner—R.E. Serwin

[57] ABSTRACT

In one exemplar embodiment, a chemiluminescent nitrogen detector for detecting chemically-bound nitrogen in an organic compound is provided in which a discrete sample of the organic compound containing the chemically-bound nitrogen is injected into a high temperature furnace where the sample is pyrolyzed at extremely high temperatures in an oxygen rich atmosphere to form nitric oxide. The pyrolysis gases, including nitric oxide is then applied to a drying means for eliminating a substantial quantity of water vapor from the carried pyrolysis gases to insure that the dew point of the gases is below the operating temperature of a nitric oxide and ozone reaction chamber. The nitric oxide and ozone are mixed in a reaction chamber to form metastable nitrogen dioxide which instantaneously relaxes to its ground state with a resulting photo-emission of light energy. The chemiluminescent detection is based on this photo-emission of light energy, and emitted light is detected by a photo-multiplier tube whose output is an electrical potential proportional to the intensity of the light detected. Appropriate electronic circuitry may be provided to convert the electrical potential output of the photo-multiplier tube to an analog electrical signal for driving a chart recorder and for application to an integrator for deriving and displaying a digital count that is proportional to the quantitative value of the chemically-bound nitrogen contained in the sample. In certain applications, a gas chromatograph may be utilized either with or without another detector, such as a thermal conductivity detector or a flame ionization detector, for detecting other chemical elements. In the case where the gas chromatograph utilizes a flame ionization detector, the furnace previously mentioned, may be eliminated as the flame ionization detector will function to pyrolyze the organic compound sample to form the necessary nitric oxide for detection.

10 Claims, 6 Drawing Figures

CHEMILUMINESCENT NITROGEN DETECTION APPARATUS AND METHOD

BACKGROUND OF THE INVENTION

This invention relates to methods and apparatus for the detection of chemically-bound nitrogen in organic compound samples. More particularly, this invention relates to the detection of chemically-bound nitrogen in an organic chemical compound utilizing chemiluminescent detection techniques.

The oldest and most widely used procedure for the analysis of chemically-bound nitrogen is the Kjeldahl method. Most often this method is used to obtain indirectly the protein content of foods and biological species. The method involves degradation and sulfation with heat, sulfuric acid and catalyst followed by neutralization, making strongly basic, distillation and titration of the ammonia. Sometimes many hours are required to perform this analysis, and there has recently been found evidence that people performing the Kjeldahl analysis on a daily basis run hazardous health risks.

Later, a titration device was devised which complemented the Kjeldahl method in that trace quantities of nitrogen could be determined accurately and quickly. This particular method involved a pyrolysis and hydrogenation of a sample at high temperatures and in the presence of a nickel catalyst. The resulting ammonia was coulometrically titrated using a four-electrode hydrogen cell. Systems based on these methods are better known as micro-coulometric titrating systems. Such an electrolytic titration apparatus is shown in the prior art as U.S. Pat. No. 3,032,493 to D. M. Couslon, et al. However, certain disadvantages of coulometric titrating methods are apparent:

1. Ultra-high purity hydrogen is required;
2. A high degree of special analytical techniques are necessary;
3. Because of the use of hydrogen at high temperatures, there are certain questionable safety features of the method;
4. A fairly low dynamic range is experienced.

More recently, chemiluminescent detection equipment for detecting chemically-bound nitrogen in the air have been developed. These chemiluminescent detectors are based on the reaction of nitric oxide with ozone to form metastable nitrogen dioxide ($NO_2^*$). Almost instantaneously the excited nitrogen dioxide relaxes to its ground state with a resulting photo-emission ($\epsilon$). Such a reaction is shown as follows:

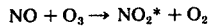

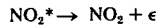

These chemiluminescent nitrogen detectors are commonly known as $NO/NO_x$ detectors. These detectors are utilized to detect ambiant nitric oxide and $NO_x$ concentrations in the air for sampling techniques and pollution control as approved by the Enviromental Protection Agency. Such $NO/NO_x$ concentration meters are presently made by several companies, but they are limited in that they are able to detect chemically-bound nitrogen only as $NO/NO_x$ gases using a chemiluminescent detection technique in gas samples or air samples. They cannot be utilized with liquid or solid organic compound samples.

Accordingly, one primary feature of the present invention is to provide a chemiluminescent detector for chemically-bound nitrogen which may be utilized with samples that may be a gas, liquid, or organic solid.

Another feature of the present invention is to provide a chemiluminescent nitrogen detector which is simple to operate and the detection results are available in a matter of minutes.

Yet another feature of the present invention is to provide a chemiluminescent nitrogen detector which can provide a digital display that is proportional to the quantity of chemically-bound nitrogen detected in the sample.

SUMMARY OF THE INVENTION

The present invention remedies the problems of the prior art by providing a source of an inert carrier gas, such as helium, or argon, a source of oxygen, a furnace or pyrolyzing means connected to both of the sources of gases for receiving the carrier gas (helium or argon), the oxygen and the organic compound containing the chemically-bound nitrogen. The furnace pyrolyzes the organic compound in an oxygen rich atmosphere to convert said chemically-bound nitrogen to nitric oxide. The nitric oxide and carrier gas are applied to a drying means for drying the gas mixture in order to lower the dew point of the carried gases below a predetermined temperature level, which is less than the operating temperature of the reaction chamber. An ozone generator is provided for generating ozone from oxygen received from the oxygen source.

A chemiluminescent detecting means receives the nitric oxide and carrier gas from the drying means and the ozone from the ozone generator for mixing in a reaction chamber. The mixing of ozone and nitric oxide causes a chemical reaction resulting in photoemission of light energy. An optical filter is provided that passes light energy in the wavelength range of 600–900 nanometers for application to a photo-multiplier tube. The photo-multiplier tube of the detecting means generates an electrical potential proportional to the intensity of the emitted light energy.

The detector can further include an electrometer connected to the photo-multiplier to amplify and generate an analog electrical signal, in response to said electrical potential, representative of the received electrical potential. A recorder or other visual display or recording means is provided for receiving the analog electrical signal from the electrometer for recording. An integrating means is also provided to receive said analog electrical signal, for integrating signals representative of nitric oxide, and displaying on a digital counter a quantitative value proportional to the quantity of nitric oxide detected.

In certain applications, a gas chromatrograph may also be utilized to receive the sample organic compound containing the chemically-bound nitrogen and the helium or argon carrier gas for chromatographically detecting elements other than nitrogen present in the compound. The helium and organic compound is then discharged into the pyrolysis furnace to pyrolyze and oxidize the organic compound to form nitric oxide for detection. Where a thermal conductivity detector is used in the gas chromatograph, elemental nitrogen may be detected.

In another embodiment, a gas chromatograph utilizing a flame ionization detector may be used. The oxygen and a source of hydrogen are applied to the flame ionization detector as well as the organic compound containing the chemically-bound nitrogen carried by the helium or other inert carrier gas except nitrogen. The flame ionization detector replaces the furnace in the preferred embodiment. However, excess water vapor must be removed from the carried gases by a moisture removing means and cooling means prior to application to the drying means and the detector reaction chamber.

BRIEF DESCRIPTION OF THE DRAWINGS

In order that the manner in which the above recited advantages and the features of the invention are attained can be understood in detail, a more particular description of the invention may be had by reference to the specific embodiments thereof which are illustrated in the appended drawings, which drawings form a part of this specification. It is to be noted, however, that the appended drawings illustrate only typical embodiments of the invention and therefore are not to be considered limiting of its scope for the invention may admit to further equally effective embodiments. In the drawings.

DETAILED DESCRIPTION OF THE PREFERRED EMBODIMENTS

Figure 1:
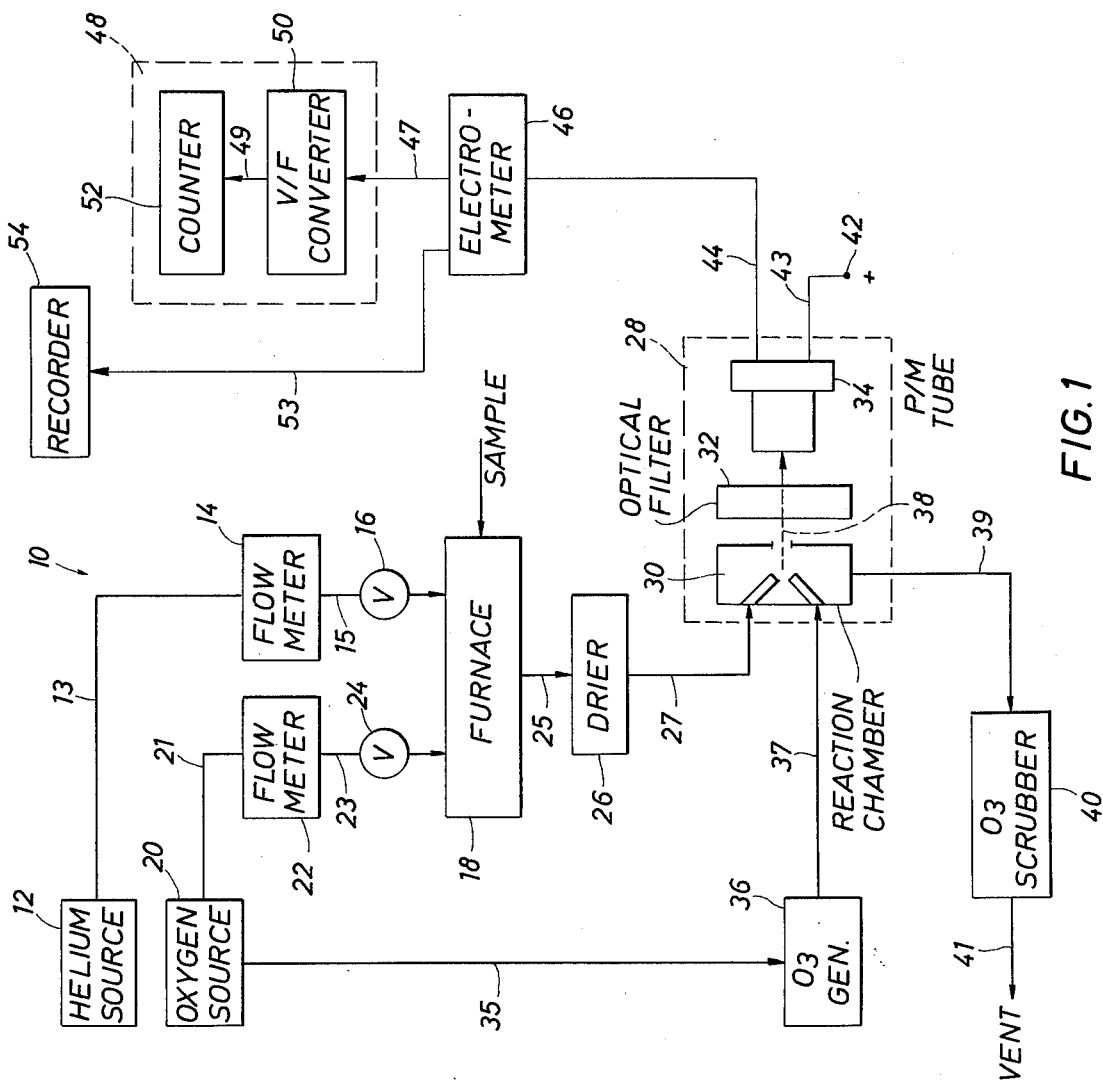
FIG. 1 is an electrical and mechanical schematic drawing of the chemiluminescent nitrogen detector according to the present invention.

Referring now to FIG. 1, a preferred embodiment of the chemiluminescent nitrogen detector is shown. The nitrogen detector is generally depicted by reference numeral 10, which comprises a helium source 12 connected by a pipe or tubing 13 through a flow meter 14, a tubing 15, and valve 16 as an input to a high temperature furnace 18. An oxygen source 20 supplies oxygen through tubing 21, flow meter 22, tubing 23, and valve 24 to a second input to furnace 18. A sample of an organic compound containing chemically bound nitrogen is inserted into the furnace to pyrolyze the organic coumpound in an oxygen-helium atmosphere to form nitric oxide by a process that will be hereinafter further described. The pyrolyzed chemical compound including nitric oxide and carried by the helium is discharged from the furnace through line 25 to a drying means 26, and then through line 27 as one input to a reaction chamber 30 of the detector module 28. Oxygen from the oxygen source 28 is also applied through tubing 35 to an ozone generator 36. The ozone generator 36 generates a supply of ozone which is applied through tubing or line 37 as a second input to the reaction chamber 30 of the detector module 28.

In the reaction chamber 30, the mixing of nitric oxide with ozone causes a reaction that forms metastable nitrogen dioxide, which almost instantaneously relaxes to its ground state with a resulting photo-emission of light energy. The light emmited by the flameless reaction travels along path 38 through an optical filter 32 which passes only wavelengths of light energy in a predetermined wavelength range, namely 600–900 nanometers. The light energy traveling along path 38 exiting from optical filter 32 is applied as an input to a photo-multiplier tube 34. The photo-multiplier tube 34 receives electrical power from a terminal 42 which is applied via lead 43 to the tube. The photomultiplier tube 34 receives the light energy traveling along path 38 and responds to the light energy by generating an amplified electrical potential proportional to the intensity of the light energy entering the photo-multiplier tube. The gas discharge from the reaction chamber 30 is applied through tubing 39 to an ozone scrubber 40, where the ozone is effectively scrubbed from the gases before the discharge gases are vented to the atmosphere through tubing 41.

The electrical potential generated by the photomultiplier tube 34 is applied through electrical conductor 44 to an electrometer 46. The electrometer receives the electrical potential from the photo-multiplier tube 34 that is proportional to the intensity of the emitted light energy from the reaction chamber 30 and generates an analog electrical signal representative of the received electrical potential. The analog electrical signal generated by the electrometer is applied through conductor 53 to a chart recorder 54 or other conventional recording means for visually recording the analog electrical signal on a strip chart, or other visual indicating means. In addition, the output of the electrometer 46 is also applied via conductor 47 as one input to a voltage/frequency converter circuit 50 of the integrator module 48. The signal from the V/F converter 50 is applied through conductors 49 to a digital counter 52 for displaying a quantitative value on the counter proportional to the quantity of nitric oxide detected in detector module 28, and therefore proportional to the quantity of chemically-bound nitrogen in the organic chemical sample.

In order to analyze chemically-bound nitrogen, the sample must be converted to a detectable species. Such a conversion is accomplished in furnace 18 which subjects the sample to a very high temperature in an oxygen rich atmosphere. It has been found that the optimum ratio of oxygen to inert carrier gas, i.e., helium, as utilized in the present invention, is 6.5 to 1. The helium merely acts as an inert carrier vehicle for carrying the nitric oxide which is used as the detectable species of nitrogen available for detection of the chemically-bound nitrogen in the sample. The oxygen is utilized in the furnace with the organic compound containing the chemically bound nitrogen to provide a source of oxygen to accomplish the following chemical conversion during pyrolysis of the organic compound:

$$R-N + O_2 \rightarrow CO_2 + H_2O + NO$$

The nitric oxide (NO) becomes the detectable species of nitrogen for detecting the chemically bound nitrogen in the organic compound sample.

Figure 4:
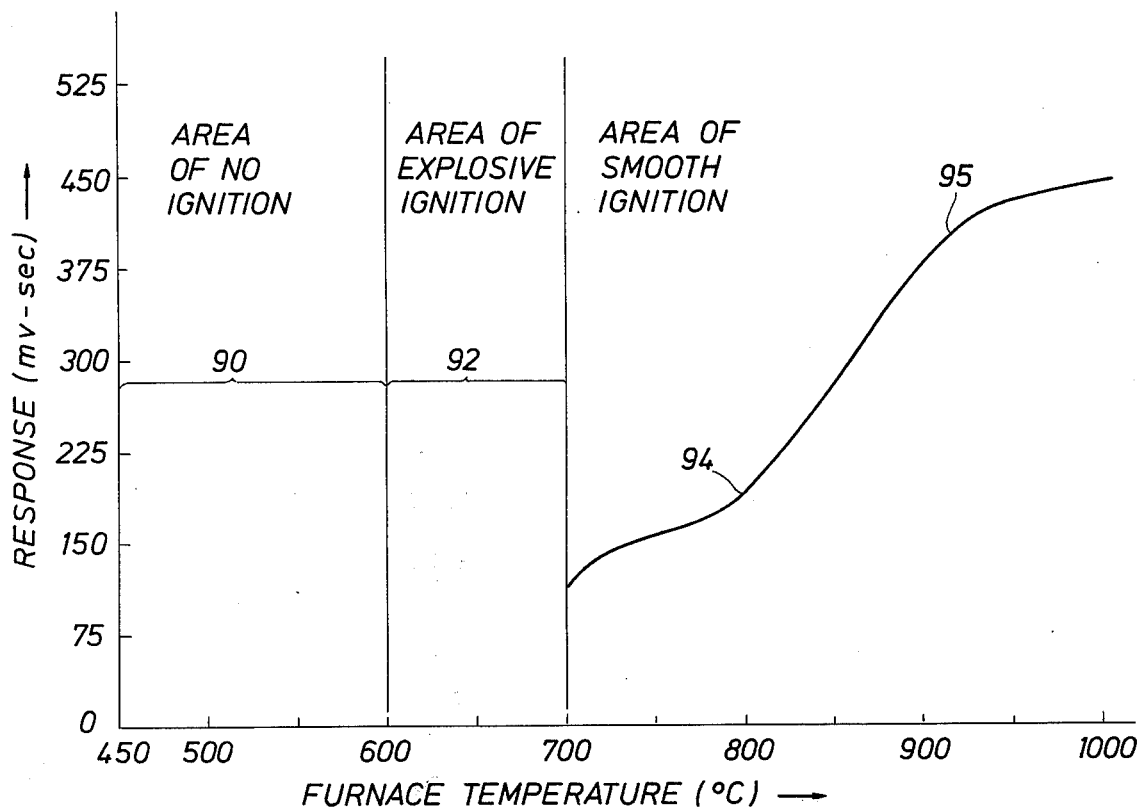
FIG. 4 is the graphical representation plotting the nitrogen detector response against furnace temperature in pyrolyzing chemical compounds to detect chemically-bound nitrogen.

As may be seen in FIG. 4, at temperatures under 600° C, no ignition or conversion of the chemically bound nitrogen (R-N) occurs as is shown in the area of the graph indicated by reference numeral 90. In the range of furnace temperatures between 600°–700° C, there is an area of explosive ignition or conversion as indicated by reference numeral 92. Above 700° C there is an area of smooth ignition or conversion of the chemically bound nitrogen (R-N) to nitric oxide as indicated by curve 94. It may be seen from the graph, and it was experimentally determined, that optimum conversion of the chemically-bound nitrogen to nitric oxide occurs above 900° C, and may be seen on that portion of curve 94 as indicated by reference number 95. Also, at 900° C or higher no conversion of the chemically-bound nitrogen or nitric oxide to either nitrogen dioxide ($NO_2$) or nitrous oxide ($N_2O$) could be detected. Since it has been determined that the optimal conversion of the chemically bound nitrogen to nitric oxide occurs above 900° C, a quartz reaction tube is utilized as a furnace 18. The quartz tube can operate continuously at such high temperatures necessary to convert the chemically bound nitrogen to nitric oxide.

The other major requirement concerning treatment of the sample before entering the detector 28 is that of moisture removal. Moisture removal from the nitric oxide and carrier gas, is accomplished by means of drying means 26. Dryer 26 functions to receive the nitric oxide and helium mixture, dries the mixture by removal of water vapor, and lowers the dew point of the carried gases below a predetermined temperature level, a level that has been determined should not exceed the operating temperature of reaction chamber 30. If a higher dew point of the gases is allowed, the gases and water vapor would temporarily fog the window of the reaction chamber 30 with resulting blockage of light to photo-multiplier tube 34. In practice it has been found that a desiccant such as magnesium perchlorate is very efficient, however, any other suitable desiccant or drying material could be utilized. The magnesium perchlorate has been found to have no noticeable nitric oxide absorption, which is important.

The detector module 28 houses a reaction chamber 30, where the ozone and nitric oxide are mixed to cause the chemiluminescent reaction. The chemiluminescent detection is based on the reaction of nitric oxide with ozone to form metastable nitrogen ($NO_2^*$). Almost instantaneously the excited nitrogen dioxide relaxes to its ground state with a resulting photo-emission ($\epsilon$). The following reactions occur:

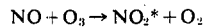

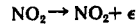

Figure 5:
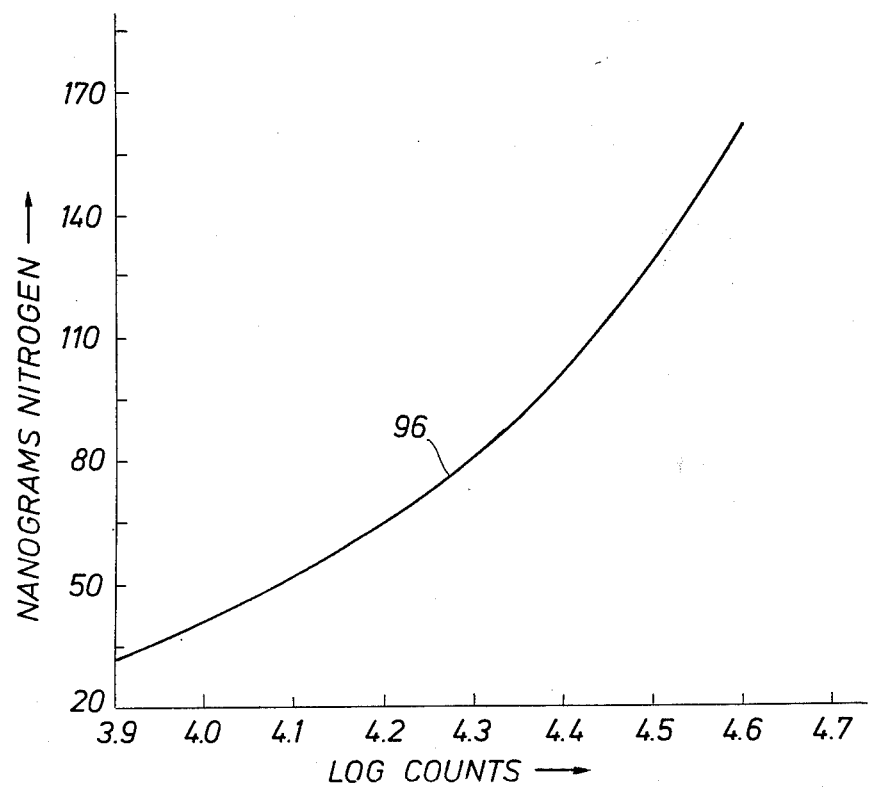
FIG. 5 is a graphical representation correlating quantitative values of nitrogen against the log of the integrator digital counter output of the nitrogen detector.

Since the basic detector unit of the detector module 28 is a photo-multiplier tube 34, the response curve of the output of the photo-multiplier tube 34 in not linear. The response is logarithmic which requires a calibration curve to correlate the output of the counter 52 of the integrator 48 to a quantitative value of chemically-bound nitrogen detected in the sample. Such a calibration curve is shown in FIG. 5 and is indicated by reference numeral 96.

Figure 6:
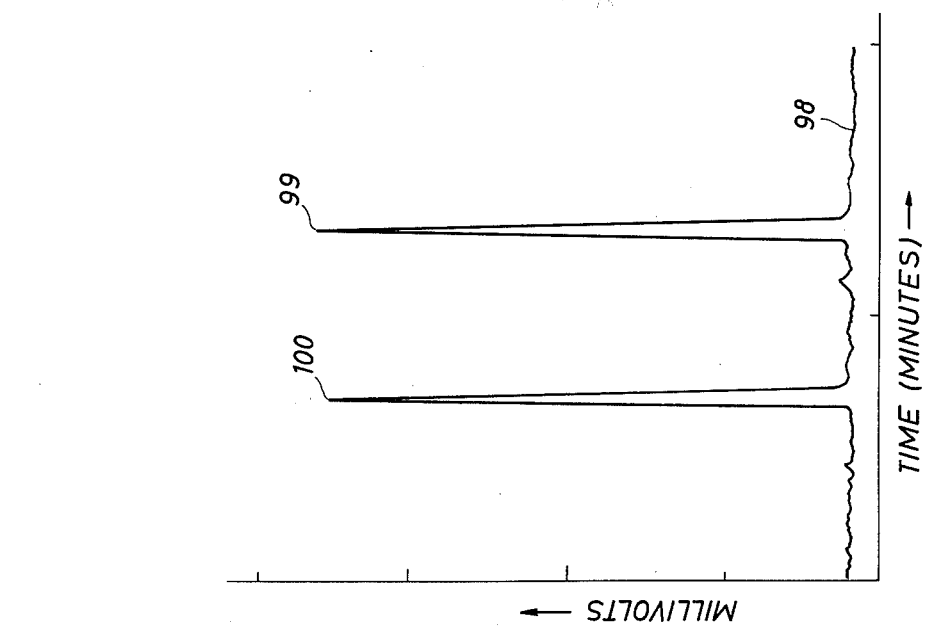
FIG. 6 is a sample or recording of the detector response in milivolts versus time showing recorded peaks illustrating the detection of chemically-bound nitrogen in samples injected into the furnace.

A typical chart recording of chemically-bound nitrogen detected in samples is shown in FIG. 6. The chart records milivolts of response versus time. The recording pin base line curve is shown at 98, and detected chemically-bound nitrogen in samples is shown at peaks 99 and 100. The counts shown on counter 52 of integrator 48 actually reflect a measure of the integration of the area under peaks 99 and 100 (see FIG. 6) as a quantitative value proportional to the quantity of chemically-bound nitrogen present in the sample. As previously mentioned, such a correlation of quantitative value shown by counter 52 to quantitative values of nitrogen in the sample are shown in a typical correlation graph or curve shown in FIG. 5.

Figure 2:
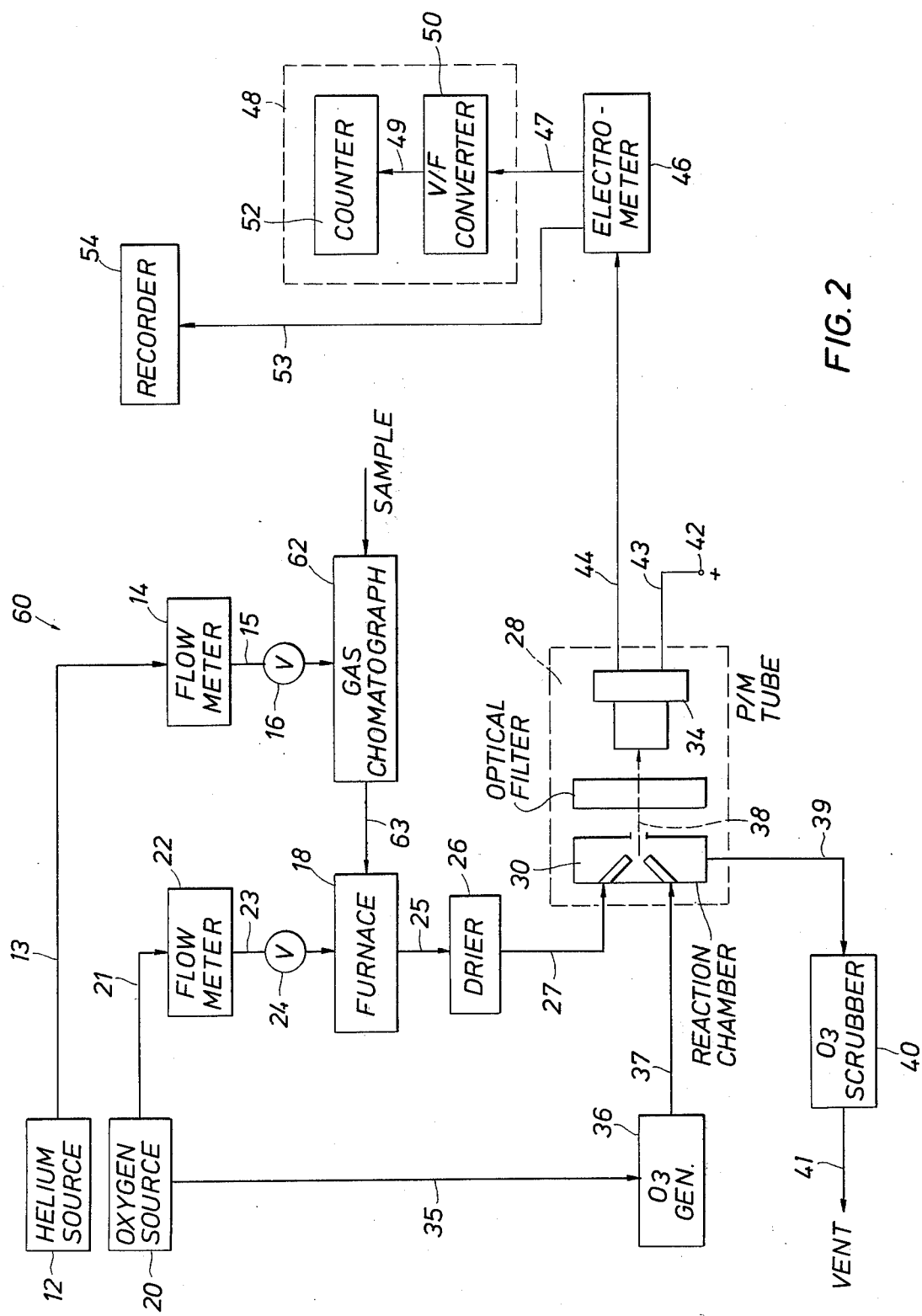
FIG. 2 is an electrical and mechanical schematic of a second embodiment of the chemiluminescent nitrogen detector.

A second embodiment of the nitrogen detector 60 is shown in FIG. 2. In this embodiment of the nitrogen detector, the carrier gas source 12 (helium) is connected by tubing 13 through a flow meter 14, tubing 15, and valve 16 to the input of a gas chromatograph 62. The sample is introduced into the gas chromatograph in conventional manner, and a chromatographic analysis of the gases in the sample may be performed utilizing thermal conductivity detection. Of primary interest is the chromatographic detection of the presence of elemental nitrogen, such as, in the analysis of air pollutants containing chemically bound and elemental nitrogen. The output of the gas column of the chromatograph 62 is applied through tubing 63 to introduce the sample gases to the input of furnace 18. Furnace 18 is identical to furnace 18 hereinabove described with regard to FIG. 1, will not be further discussed. Oxygen is supplied from oxygen source 20 through tubing 21, flow meter 22, tubing 23 and valve 24 as an input to the furnace 18 for providing an oxygen rich atmosphere for maximum conversion of the chemically-bound nitrogen in the sample to nitric oxide, as hereinabove described with regard to FIG. 1. The remaining portions of the schematic shown in FIG. 2, namely the application of the nitric oxide and its carrier gas, helium, as applied through dryer 26 to the detector module 28, the generation of ozone by ozone generator 36 from oxygen from oxygen source 20, and application of the ozone to the detector module 28 are identical to the functions performed by the blocks having the identical reference numbers and therefore will not be hereinafter further described. The ozone scrubber 40 also performs the identical function as the ozone scrubber discussed with regard to the first embodiment shown in FIG. 1.

The function of the reaction chamber 30, optical filter 32, and photo-multiplier 34 are identical to the functions of the identically referenced units of detector module 28 as hereinabove described with regard to the first embodiment shown in FIG. 1 and will not be further elaborated on herein. Similarly, the application of the photo-multiplier tube 34 output through electrometer 46, the recording of the electrometer output by recorder 54, and the integration and display of the electrometer output by integrator 48 and counter 52 are identical to the functions hereinabove described regarding the first embodiment as shown in FIG. 1 and need not be further described.

Figure 3:
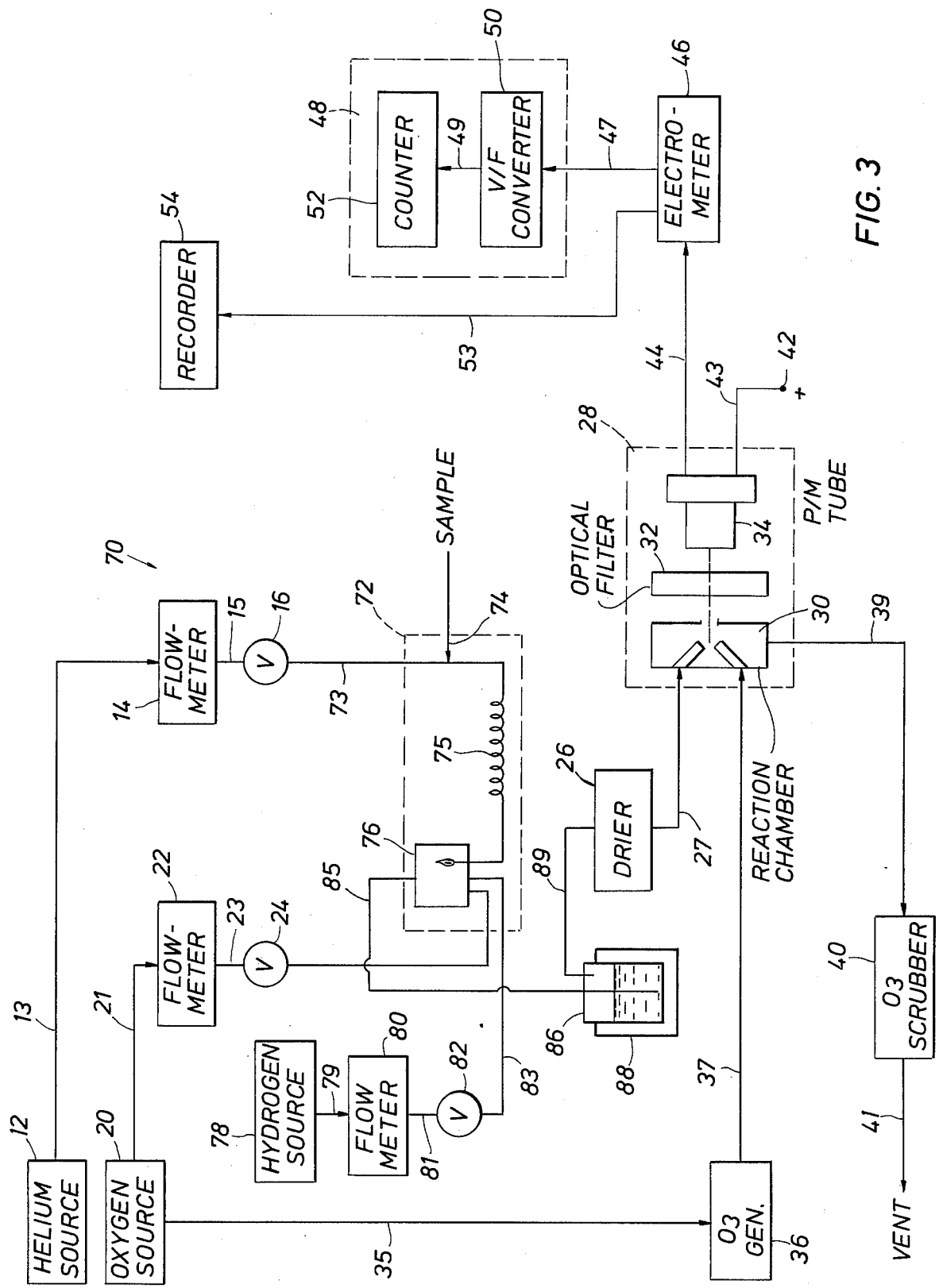
FIG. 3 is an electrical and mechanical schematic of a third embodiment of the chemiluminescent nitrogen detector.

In FIG. 3, a third embodiment of the nitrogen detector 70 is shown. Nitrogen detector 70 comprises a carrier gas source 12 which applies carrier gas helium through line 13, flow meter 14, tubing 15, valve 16, and tubing 73 to the input of a chromatograph column 75 of a gas chromatograph 72. The sample is introduced through 74 into the chromatograph column 75. The output of the chromatograph column 75 is applied as an input to a flame ionization detector 76. Oxygen from oxygen source 20 is applied through tubing 21, flow meter 22, tubing 23, valve 24, and tubing 77 as a second input to the flame ionization detector 76. In addition, a hydrogen from hydrogen source 78 is applied through line 79, flow meter 80, line 81, valve 82, and tubing 83 as a third input to the flame ionization detector 76. Flame ionization detector 76 may be of any conventional gas chromatograph flame ionization detector. Pyrolysis of the chemical compound carrying the chemically-bound nitrogen occurs in flame ionization detector 76, thus eliminating the need for furnace 18 as shown in previous two embodiments illustrated above in FIGS. 1 and 2.

The output of the flame ionization detector 76 now containing nitric oxide, other gases and the helium as a carrier is applied through tubing 85 as an input to a water vapor removal means 86, which may conveniently be a water trap, for removing water vapor from the carried gases. A cooling means 88 is provided to cool the hot gases and cause the water vapor to condense in the moisture trapping means 86. The output of the moisture trap 86 is through a tubing 89 as an input to a conventional drying means 26. The drying means 26 is identical to the drying means 26 illustrated in FIGS. 1 and 2 with regard to the first two embodiments and need not be further described. The output of the drying means 26 is applied through a tubing 27 as one input to reaction chamber 30 of the detector module 28. The ozone generator 36, ozone scrubber 40 and detector 28 are identical to those units hereinabove described with regard to previous embodiments shown in FIGS. 1 and 2, and need not be further described. Similarly, the recording and display electronics comprising electrometer 46, recorder 54, and integrator 48 all function in an identical manner to their counterparts of same reference number shown in FIGS. 1 and 2 and need not be herein further described.

In the preferred embodiment of FIG. 1, the various modules and units identified in the block diagram can conveniently be comprised of the following commercially available equipment:

| | |
|---|---|
| Furnace 18 | Antek Instruments, Inc. Model 771 pyro-reactor |
| Ozone generator 36 | McMillan Electronics Corp. Part no. 1200350 |
| Ozone scrubber 40 | McMillan Electronics Corp. Part No. 0045 |
| Detector module 28 | McMillan Electronics Corp. Detector assembly of model 2200 $NO/NO_x$ meter |
| V/F Convertor 50 | Burr Brown Co. No. VFC-12 |
| Counter 52 | Antek Instruments, Inc. Part No. 1893A |
| Electrometer 46 | McMillan Electronics Corp. Part No. 210-052 |

Of course, other suitable conventional circuits and apparatus may be substituted for the blocks of the block diagrams of FIGS. 1–3.

Numerous variations and modifications may obviously be made in the structure herein described without departing from the present invention. Accordingly, it should be clearly understood that the forms of the invention herein described and shown in the Figures of the accompanying drawings are illustrative only and are not intended to limit the scope of the invention.

What is claimed is:

1. The method for determining the total chemically combined nitrogen content of a sample comprising the steps:
    a. decomposing said sample in one step in the presence of an oxygen-rich atmosphere of oxygen and an inert gas and at a temperature sufficiently above 700° C. that substantially all of the chemically bound nitrogen is recovered as nitric oxide (NO), such decomposition being conducted in the absence of a catalyst,
    b. causing the nitric oxide produced by such decomposition to undergo a chemiluminescent reaction with ozone, and
    c. determining the magnitude of the chemiluminescent reaction to indicate the quantity of chemically combined nitrogen in said sample.

2. The method of claim 1 wherein said temperature is in excess of 900° C.

3. The method of claim 1 which includes the further step of chromatographically detecting constituents of the sample prior to decomposing the same and thereafter determining the nitrogen content of the sample as aforesaid.

4. The method of claim 2 which includes the further step of chromatographically detecting constituents of the sample prior to decomposing the same and thereafter determining the nitrogen content of the sample as aforesaid.

5. The method of claim 1 wherein the magnitude of the chemiluminescent reaction is determined within the range of 600 to 900 nanometers.

6. The method of determining the total nitrogen content of a sample of material containing organically bound nitrogen comprising the steps of
    a. heating said sample in the presence of an oxygen-rich atmosphere of oxygen and an inert gas to a temperature sufficiently above 700° C that substantially all of the bound nitrogen is converted to nitric oxide (NO) in a single step, such heating being conducted in the absence of a catalyst,
    b. causing the nitric oxide produced by such heating to undergo a chemiluminescent reaction with ozone, and
    c. determining the magnitude of the chemiluminescent reaction to indicate the quantity of bound nitrogen in said sample.

7. The method of claim 6 wherein said temperature is in excess of 900° C.

8. The method of claim 6 which includes the further step of chromatographically detecting constituents of the sample prior to heating the same as aforesaid.

9. The method of claim 7 which includes the further step of chromatographically detecting constituents of the sample prior to heating the same as aforesaid.

10. The method of claim 6 wherein the mangitude of the chemiluminescent reaction is determined within the range of 600 to 900 nanometers.

* * * * *